US012286417B2

(12) United States Patent
Sumi et al.

(10) Patent No.: US 12,286,417 B2
(45) Date of Patent: Apr. 29, 2025

(54) 1,4-DIAZOCANE COMPOUND OR SALT THEREOF

(71) Applicant: D. WESTERN THERAPEUTICS INSTITUTE, INC., Nagoya (JP)

(72) Inventors: Kengo Sumi, Nagoya (JP); Tomoyuki Koide, Chuo-ku (JP); Osamu Kimata, Chuo-ku (JP); Yuji Takashima, Chuo-ku (JP); Kazunao Masubuchi, Chuo-ku (JP)

(73) Assignee: D. WESTERN THERAPEUTICS INSTITUTE, INC., Nagoya (JP)

( * ) Notice: Subject to any disclaimer, the term of this patent is extended or adjusted under 35 U.S.C. 154(b) by 936 days.

(21) Appl. No.: 17/290,306

(22) PCT Filed: Nov. 1, 2019

(86) PCT No.: PCT/JP2019/043068
§ 371 (c)(1),
(2) Date: Apr. 30, 2021

(87) PCT Pub. No.: WO2020/091054
PCT Pub. Date: May 7, 2020

(65) Prior Publication Data
US 2021/0371396 A1 Dec. 2, 2021

(30) Foreign Application Priority Data
Nov. 1, 2018 (JP) .................................. 2018-206941

(51) Int. Cl.
*C07D 401/12* (2006.01)
(52) U.S. Cl.
CPC .................................. *C07D 401/12* (2013.01)
(58) Field of Classification Search
None
See application file for complete search history.

(56) References Cited

U.S. PATENT DOCUMENTS

2008/0064681 A1  3/2008  Hidaka et al.
2012/0035159 A1  2/2012  Hidaka et al.

FOREIGN PATENT DOCUMENTS

CN   102448941 A   5/2012
CN   105906609 A   8/2016
JP     4915010 B2   2/2012

OTHER PUBLICATIONS

International Search Report issued on Jan. 21, 2020 in PCT/JP2019/043068 filed on Nov. 1, 2019, citing documents AA, AB, AM and AO-AY therein, 3 pages.
File Registry on STN, RN 1824139-45-8, 2015, 1 total page.
File Registry on STN, RN 1932491-82-1, 2016, 1 total page.
File Registry on STN, RN 1932077-61-6, 2016, 1 total page.
File Registry on STN, RN 1896105-17-1, 2016, 1 total page.
File Registry on STN, RN 1890622-72-6, 2016, 1 total page.
File Registry on STN, RN 1892420-96-0, 2016, 1 total page.
File Registry on STN, RN 1824339-52-7, 2015, 1 total page.
File Registry on STN, RN 1563605-04-8, 2014, 1 total page.
Greene, T. W. et al., "Protective Groups in Organic Synthesis," Third Edition, John Wiley & Sons, Inc., 1999, pp. 518-525, 573, 574, 579, 580, 14 total pages.
Sumi, K. et al., "IOP-lowering effect of isoquinoline-5-sulfonamide compounds in ocular normotensive monkeys," Bioorganic & Medicinal Chemistry Letters, vol. 24, 2014, pp. 831-834.
Li, J. J., "Name Reactions a Collection of Detailed Reaction Mechanisms," Second Edition, Springer, 2003, p. 265, 3 total pages.
Combined Chinese Office Action and Search Report issued Aug. 25, 2022, in Chinese Patent Application No. 201980072481.8 (with English translation), citing documents 15-16 and 24 therein.
STN Database, Registry CAS RN 1932491-82-1, Jun. 15, 2016, 6 pages.

*Primary Examiner* — Noble E Jarrell
(74) *Attorney, Agent, or Firm* — Oblon, McClelland, Maier & Neustadt, L.L.P.

(57) ABSTRACT

A method may produce an isoquinoline-6-sulfonamide derivative useful as a medicinal drug; and an intermediate which is used for the method, and more specifically, a 1,4-diazocane compound of formula (8), wherein $R^4$ is an amino protecting group, or a salt thereof.

2 Claims, No Drawings

1,4-DIAZOCANE COMPOUND OR SALT THEREOF

CROSS REFERENCE TO RELATED APPLICATIONS

The present application is the national stage of international application PCT/JP2019/043068, filed on Nov. 1, 2019, and claims the benefit of the filing date of Japanese Appl. No. 2018-206941, filed on Nov. 1, 2018, the content of each of which is incorporated by reference.

FIELD OF THE INVENTION

The present invention relates to a 1,4-diazocane compound useful as a synthetic intermediate for medicinal drugs, and use thereof.

BACKGROUND OF THE INVENTION

Compounds in which a nitrogen-containing saturated heterocyclic ring such as diazocane binds to an isoquinoline ring at the 6-position through a sulfonyl group are known to have a potent ocular hypotensive action and be useful as therapeutic drugs for ocular hypertension such as glaucoma (Patent Literature 1). Of these isoquinoline-6-sulfonamide derivatives, (R)-6-(2-methyl-1,4-diazocan-1-ylsulfonyl)isoquinoline of formula (I):

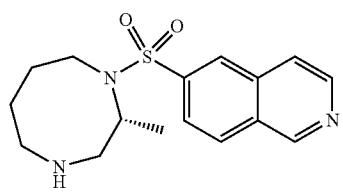

(I)

or a salt thereof is known to have a particularly excellent ocular hypotensive action and be useful as a therapeutic drug for glaucoma or ocular hypertension. Patent Literature 1 indicates that the compound can be produced in accordance with the following reaction formula.

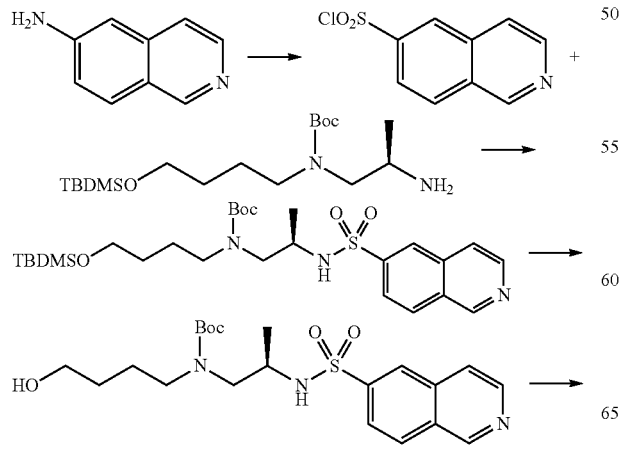

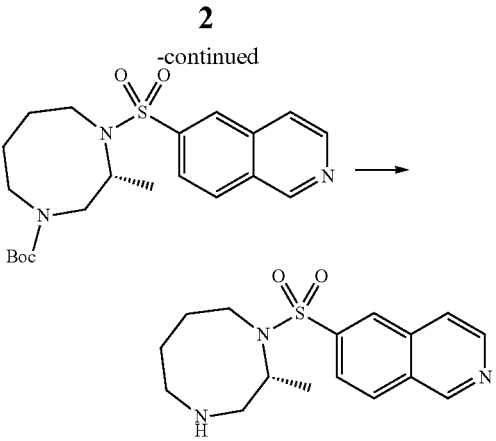

CITATION LIST

Patent Literature

Patent Literature 1: JP-B-4915010

SUMMARY OF THE INVENTION

Technical Problem

However, the method for producing a compound (I) according to Patent Literature 1 has the problem that the yields in reaction of isoquinoline-6-sulfonyl chloride with a diamine compound and subsequent 1,4-diazocane-forming reaction are low, resulting in increased production cost, and a step of purification by column chromatography is necessary. Thus, the method is not satisfactory as an industrial method for producing a medicinal drug product.

Accordingly, an object of the present invention is to provide a novel method for producing a compound of formula (I) via a novel intermediate.

Solution to Problem

Thus, the present inventors conducted studies for developing a novel method for producing a compound of formula (I), and resultantly successfully synthesized a novel 1,4-diazocane compound having an amino protecting group, and found that use of the compound enables production of a compound of formula (I) in high yield. In this way, the present invention was completed.

That is, the present invention relates to the following aspects [1] to [5].

[1] A 1,4-diazocane compound of formula (A):

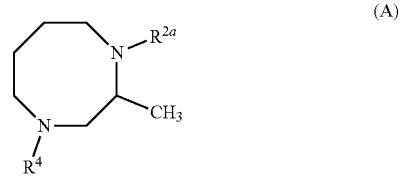

(A)

or a salt thereof, wherein $R^{2a}$ represents a hydrogen atom or an amino protecting group and $R^4$ represents an amino protecting group.

[2] A compound of formula (B):

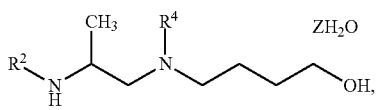

a salt thereof or a hydrate thereof,
wherein $R^2$ represents an amino protecting group, $R^4$ represents a hydrogen atom or an amino protecting group and Z represents a number of from 0 to 1.

[3] A method for producing an isoquinoline-6-sulfonamide derivative of formula (11):

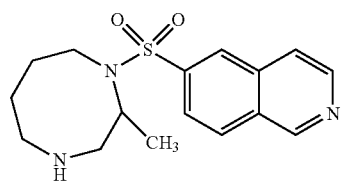

or a salt thereof, the method comprising reacting a 1,4-diazocane compound of formula (8):

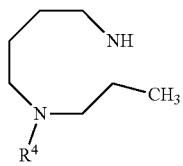

or a salt thereof, wherein $R^4$ represents an amino protecting group, with an isoquinoline-6-sulfonyl halide of formula (9):

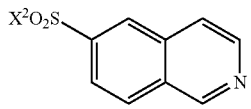

or a salt thereof, wherein $X^2$ represents a halogen atom, and then carrying out an elimination reaction of amino protecting group.

[4] A method for producing a 1,4-diazocane compound of formula (A):

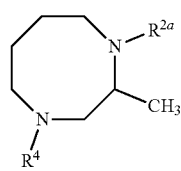

or a salt thereof, wherein $R^{2a}$ represents a hydrogen atom or an amino protecting group and $R^4$ represents an amino protecting group, the method comprising reacting a compound of formula (6):

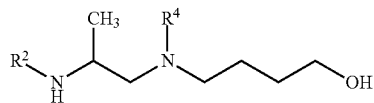

wherein $R^2$ and $R^4$ each represent an amino protecting group,
with an azodicarboxylic acid ester and triphenylphosphine, and then carrying out an elimination reaction of amino protecting group if necessary.

[5] A method for producing a compound of formula (B):

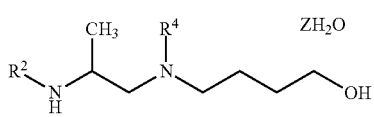

wherein $R^2$ represents an amino protecting group, $R^4$ represents a hydrogen atom or an amino protecting group and Z represents a number of from 0 to 1,
, a salt thereof or a hydrate thereof, the method comprising reacting a compound of formula (3):

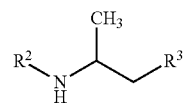

wherein $R^2$ represents an amino protecting group and $R^3$ represents a halogen atom or a substituted sulfonyloxy group,
with 4-amino-1-butanol, and then protecting the amino group if necessary.

Advantageous Effect of the Invention

According to the present invention, a compound of formula (A) or a salt thereof can be produced in high yield from inexpensive raw materials.

DETAILED DESCRIPTION OF THE INVENTION

A 1,4-diazocane compound of formula (A) or a salt thereof is useful as an intermediate for production of an isoquinoline-6-sulfonamide derivative of formula (11) or a salt thereof.

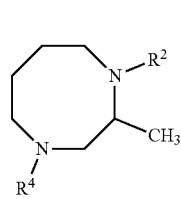

In formula (A), $R^{2a}$ represents a hydrogen atom or an amino protecting group. The amino protecting group of $R^{2a}$ may be a protecting group capable of being eliminated under conditions different from those for the amino protecting group of $R^4$, and is preferably a nitrobenzenesulfonyl group which acts also as an amino group activating group, from the viewpoint of forming a 1,4-diazocane ring by Mitsunobu reaction of aminoalcohol. Here, examples of the nitrobenzenesulfonyl group include 2-nitrobenzenesulfonyl group (Ns), 4-nitrobenzenesulfonyl group (Nos) and 2,4-dinitrobenzenesulfonyl group (DNs). $R^{2a}$ is more preferably a hydrogen atom.

Examples of the amino protecting group of $R^4$ include carbamate-based protecting groups such as t-butoxycarbonyl group (Boc), benzyloxycarbonyl group (Cbz), 9-fluorenylmethylcarbonyl group (Fmoc), 2,2,2-trichloroethoxycarbonyl group (Troc) and allyloxycarbonyl group; amide-based protecting groups such as trifluoroacetyl group; phthaloyl group; and p-toluenesulfonyl group. From the viewpoint of ease of deprotection, carbamate-based protecting groups are preferable, and the t-butoxycarbonyl group (Boc) is more preferable.

Of compounds of formula (A), steric isomers of formula (A1) are particularly preferable.

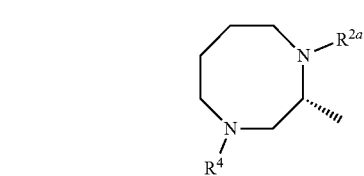

(A1)

wherein $R^{2a}$ and $R^4$ are the same as described above.

Here, Rea is more preferably a hydrogen atom.

A compound of formula (B), a salt thereof or a hydrate thereof is useful as an intermediate for production of a compound of formula (A) or a salt thereof.

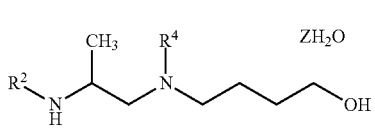

(B)

In formula (B), $R^2$ represents an amino protecting group. The amino protecting group of $R^2$ may be a protecting group capable of being eliminated under conditions different from those for the amino protecting group of $R^4$, and is preferably nitrobenzenesulfonyl group which acts also as an amino group activating group, from the viewpoint of forming a 1,4-diazocane ring by Mitsunobu reaction of aminoalcohol. Here, examples of the nitrobenzenesulfonyl group include 2-nitrobenzenesulfonyl group (Ns), 4-nitrobenzenesulfonyl group (Nos) and 2,4-dinitrobenzenesulfonyl group (DNs). $R^4$ represents a hydrogen atom or an amino protecting group, and is preferably the same as described above. Z is preferably a number of from 0 to 1.

Of compounds of formula (B), steric isomers of formula (B1):

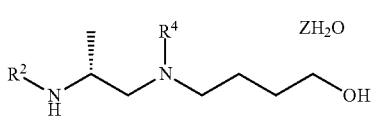

(B1)

wherein $R^2$, $R^4$ and Z are the same as described above, are particularly preferable.

The production method in the present invention can be represented by the following reaction formulae which show the reactions beginning with a starting material.

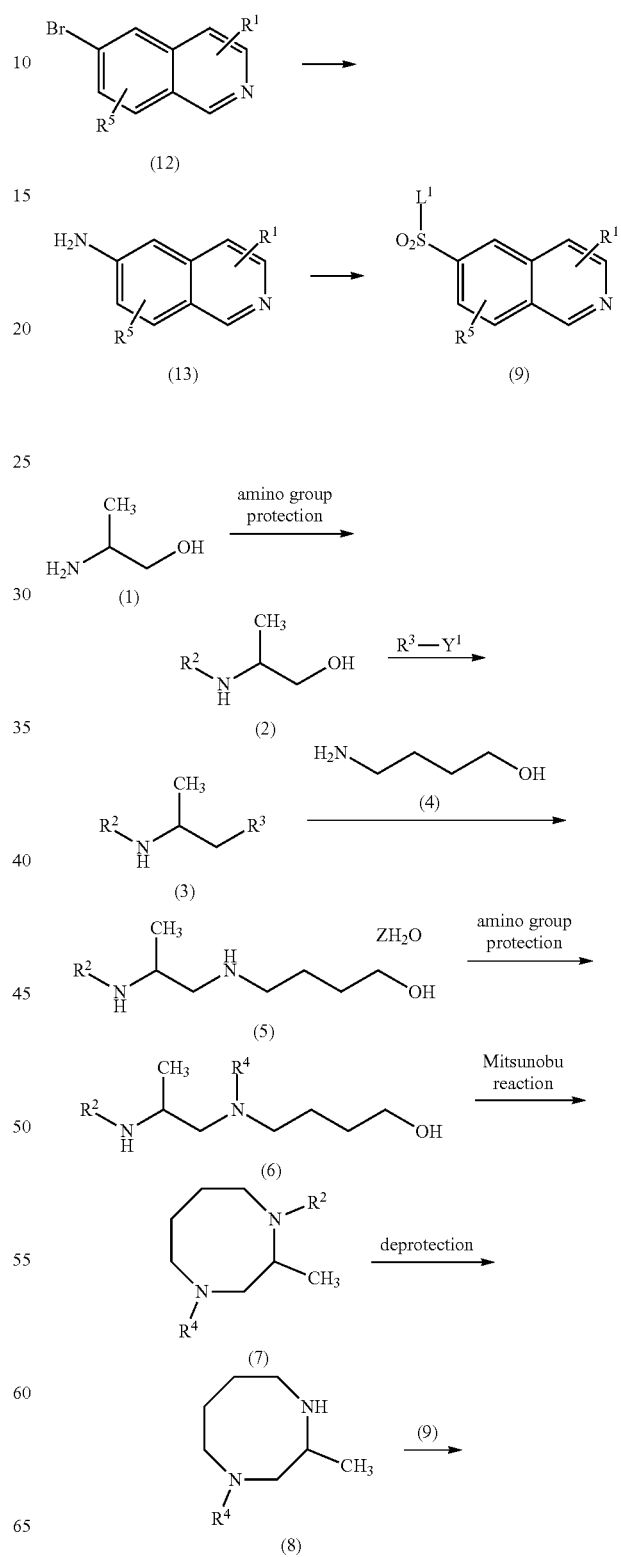

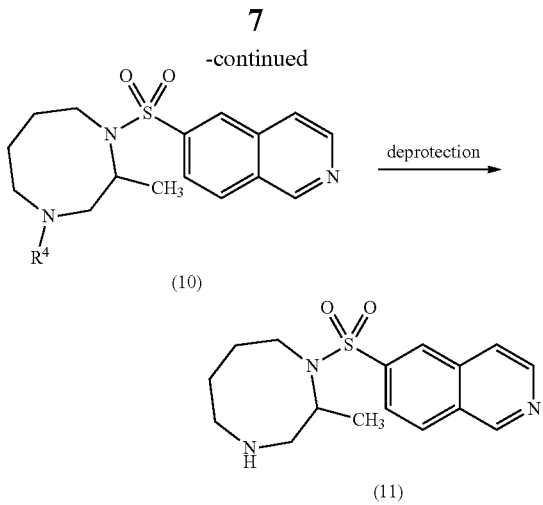

(10)

(11)

wherein $R^1$ and $R^5$ each independently represent a hydrogen atom, a halogen atom, a cyano group, an alkyl group, a halogenoalkyl group, an alkenyl group, an alkoxy group, an alkylthio group, a hydroxy group, a mercapto group, a nitro group, an aryl group, an amino group or an aminoalkylthio group, $R^2$ represents an amino protecting group, $R^3$ represents a substituted sulfonyloxy group or a halogen atom, $L^1$ represents a halogen atom, a hydroxy group or a leaving group, $Y^1$ represents a halogen atom or a sulfinyl group, $R^4$ represents an amino protecting group, and Z represents a number of from 0 to 1.

Each reaction step will be described below.

(1) Step of Producing Compound (9)

Compound (9) can be produced using commercially available 6-aminoisoquinoline (13) or 6-bromoisoquinoline (12). For synthesis of compound (9) from compound (12), a known method can be used.

(2) Step of Producing Compound (2) from Compound (1)

Preferably, (R)-2-amino-1-propanol is used as compound (1). The reagent used for protecting the amino of compound (1) is preferably a nitrobenzenesulfonyl halide such as nitrobenzenesulfonyl chloride as described above.

Preferably, this reaction is carried out in the presence of an aromatic amine such as pyridine, or a tertiary amine such as triethylamine, dimethylaniline or diisopropylethylamine. The amount of the amine used is preferably from 1 to 5 times, more preferably from 1 to 3 times a mole of compound (1). Preferably, an ether-based solvent such as tetrahydrofuran, diethyl ether, dioxane or cyclopentylmethyl ether, a polar solvent such as acetonitrile, or an aromatic hydrocarbon-based solvent such as toluene is used as a reaction solvent. The reaction may be carried out at from −10° C. to 50° C. for from 1 hour to 12 hours.

(3) Step of Producing Compound (3) from Compound (2)

Examples of $R^3$—$Y^1$ which is reacted with compound (2) include substituted sulfonyl halides and thionyl halides. Examples of the substituted sulfonyl halides include alkanesulfonyl halides such as methanesulfonyl halides, and arylsulfonyl halides such as p-toluenesulfonyl halides. Examples of the thionyl halides include thionyl chloride and thionyl bromide.

Preferably, the reaction of compound (2) with substituted sulfonyl halide is carried out in the presence of, for example, an aromatic amine such as pyridine or a tertiary amine such as triethylamine or dimethylaniline. The amount of the amine used is preferably from 1 to 5 times, more preferably from 1 to 3 times a mole of compound (2). Preferably, an ether-based solvent such as tetrahydrofuran, diethyl ether or dioxane, a polar solvent such as acetonitrile, or an aromatic hydrocarbon-based solvent such as toluene is used as a solvent for the reaction. The reaction may be carried out at from 0° C. to 100° C. for from 1 hour to 12 hours.

Preferably, the reaction of compound (2) with a thionyl halide such as thionyl chloride is carried out at from 60 to 80° C. for from 3 to 24 hours in the presence of an aromatic hydrocarbon-based solvent such as toluene or xylene, or an aromatic amine such as pyridine.

(4) Step of Producing Compound (5) from Compound (3)

Compound (5) can be produced by reacting compound (3) with 4-amino-1-butanol (4). Preferably, the reaction is carried out in the present of a base. As the base, an alkali metal carbonate such as potassium carbonate or sodium carbonate, or an alkali metal hydroxide such as potassium hydroxide or sodium hydroxide can be used. The amount of the base used is preferably from 1 to 10 times, more preferably from 1 to 5 times a mole of compound (3). Preferably, a polar solvent such as acetonitrile is used as a reaction solvent. The reaction may be carried out at from 10° C. to 150° C. for from 1 hour to 12 hours. Compound (5) can be isolated in a hydrate form.

(5) Step of Producing Compound (6) from Compound (5)

Compound (6) can be obtained by protecting the amino group of compound (5). As a compound used for protecting the amino group of compound (5), a compound corresponding to the amino protecting group of $R^4$ is used. For example, when the amino group is protected with a t-butoxycarbonyl group, di-t-butyl dicarbonate is used. Preferably, reaction for introduction of the protecting group is carried out in the presence of an aromatic amine such as pyridine, or a tertiary amine such as triethylamine or dimethylaniline. The amount of the amine used is preferably from 1 to 10 times, more preferably from 1 to 3 times a mole of compound (5). As a reaction solvent, halogenated hydrocarbon-based solvents such as dichloromethane, alcohol-based solvents such as methanol, ether-based solvents such as tetrahydrofuran and diethyl ether, nitrile-based solvents such as acetonitrile, water and the like, or a mixture of any of these solvents at an appropriate ration is used. The reaction may be carried out at from 0° C. to 150° C. for from 1 hour to 12 hours.

(6) Step of Producing Compound (7) from Compound (6)

Preferably, Mitsunobu reaction is utilized for the method for producing compound (7) by cyclizing compound (6). That is, compound (7) is obtained by reacting compound (6) with an azodicarboxylic acid ester and triphenyl phosphine.

Examples of the azodicarboxylic acid ester include azodicarboxylic acid alkyl esters such as diisopropyl azodicarboxylate and diethyl azodicarboxylate. The amount of the azodicarboxylic acid ester used is preferably from 1 to 5 times, more preferably from 1 to 3 times a mole of compound (6). The amount of triphenylphosphine used is preferably from 1 to 5 times, more preferably from 1 to 3 times a mole of compound (6). The reaction may be carried out at from 0 to 100° C. for from 1 to 12 hours in an ether-based solvent such as tetrahydrofuran or an aromatic hydrocarbon-based solvent such as toluene.

(7) Step of Producing Compound (8) from Compound (7)

Compound (8) can be obtained by eliminating the amino protecting group $R^2$ of compound (7).

Elimination means such as a base or reduction can be selected according to the type of the amino protecting group of $R^2$. For example, when $R^2$ is a nitrobenzenesulfonyl group, deprotection can be performed under mild conditions by reaction of a thiol such as thiophenol or dodecanthiol. An alkanethiol with a long-chain alkyl such as dodecanthiol is preferable because it is less odorous. The amount of the thiol used is preferably from 1 to 5 times, more preferably from 1 to 3 times a mole of compound (7). Preferably, deprotection reaction is carried out in the presence of a base such as potassium carbonate, sodium carbonate, lithium hydroxide or a hydrate thereof. The amount of the base used is preferably from 1 to 20 times, more preferably from 1 to 10 times a mole of compound (7). The reaction may be carried out at room temperature to 100° C. for from 30 minutes to 5 hours in a solvent such as a polar solvent such as acetonitrile or dimethylformamide, or an aromatic hydrocarbon-based solvent such as toluene.

(8) Step of Producing Compound (10) by Reacting Compound (8) with Compound (9)

Compound (10) can be obtained by reacting compound (8) with an isoquinoline-6-sulfonyl halide or an acid addition salt thereof (9). Preferably, the reaction is carried out in the presence of an aromatic amine such as pyridine, or an amine such as triethylamine, dimethylaniline or dimethylaminopyridine. The amount of the tertiary amine used is preferably from 1 to 5 times, more preferably from 1 to 3 times a mole of compound (8). The reaction can be carried out in a polar solvent such as acetonitrile or dimethylformamide, or an aromatic hydrocarbon-based solvent such as toluene. As reaction conditions, the reaction may be carried out at from 0 to 100° C. for from 1 to 5 hours.

(9) Step of Producing Compound (11) from Compound (10)

Compound (11) can be obtained by eliminating the amino protecting group ($R^4$) of compound (10). For deprotection reaction of $R^4$, means such as a base, an acid or reduction can be selected according to the type of $R^4$. For example, when $R^4$ is a t-butoxycarbonyl group, deprotection may be performed under acidic conditions. For establishing acidic conditions, a mineral acid such as hydrochloric acid or sulfuric acid, or a strong acid such as trifluoroacetic acid can be used. For deprotection of the benzyloxycarbonyl group, hydrogenation reaction using a palladium catalyst, Birch reduction or the like can be employed. The deprotection reaction may be carried out at from 0 to 150° C. for from 1 hour to 20 hours in, for example, an ether-based solvent such as dioxane, an aromatic hydrocarbon-based solvent such as toluene, or an ester-based solvent such as ethyl acetate.

Preferably, compound (11) is isolated as an acid addition salt such as a hydrochloride or a sulfate. Particularly preferably, compound (11) is isolated as a hydrochloride from the viewpoint of use as a medicinal drug product. For isolating compound (11) as an acid addition salt, it is preferable that in an organic solvent, an acid such as hydrochloric acid be added to form an acid addition salt. For example, when compound (11) is isolated as a hydrochloride, a hydrochloride of compound (11) can be obtained efficiently.

According to the method of the present invention, compound (11) or an acid addition salt thereof, which is useful as a medicinal drug, can be industrially advantageously obtained.

EXAMPLES

The present invention will now be described in more detail by way of Examples.

Example 1

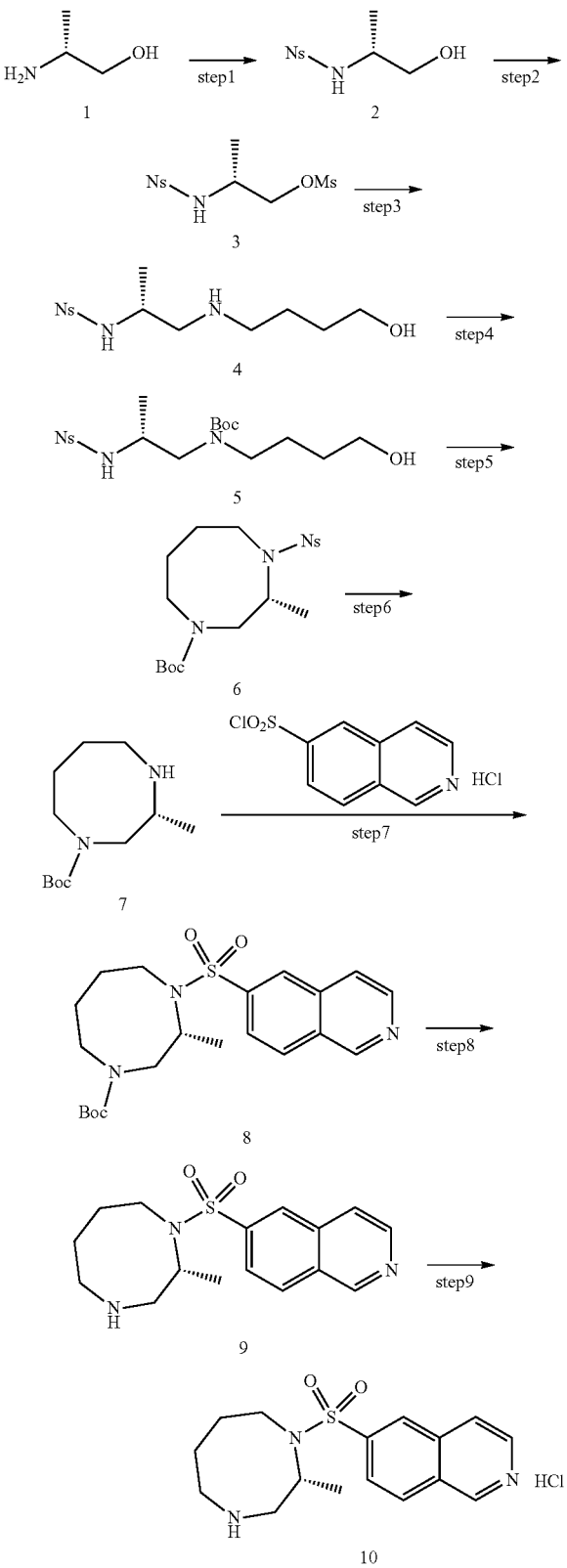

(1) Steps 1 and 2

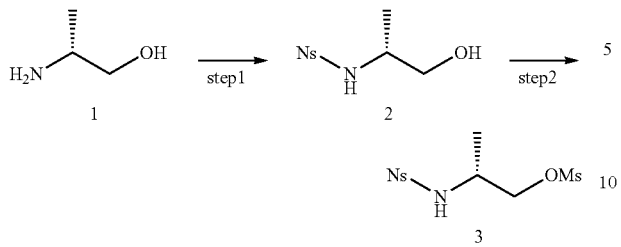

(R)-2-amino-1-propanol (3.82 g) was dissolved in THF (150 mL), triethylamine (7.08 mL) and 2-nitrobenzenesulfonyl chloride (11.2 g) were added at 0° C., and the mixture was stirred at room temperature for 2 hours. Disappearance of the raw material was confirmed by TLC, distilled water was then added, and the mixture was extracted with ethyl acetate. The organic layer was washed with saturated saline, and dried with anhydrous sodium sulfate. Filtration was performed, and the filtrate was concentrated under reduced pressure to obtain (R)—N-(2-hydroxy-1-methylethyl)-2-nitrobenzenesulfonamide in the form of a white solid (13.4 g). To this was added THF (150 mL) to dissolve the white solid, triethylamine (7.08 mL) and methanesulfonyl chloride (3.93 mL) were then added at 0° C., and the mixture was stirred at room temperature for 2 hours. Disappearance of the raw material was confirmed by TLC, distilled water was then added, and the mixture was extracted with ethyl acetate. The organic layer was washed with saturated saline, and dried with anhydrous sodium sulfate. Filtration was performed, and the filtrate was concentrated under reduced pressure. The obtained solid was washed with n-hexane/ethyl acetate=8/1 to obtain (R)—N-(1-methanesulfonyloxypropan-2-yl)-2-nitrobenzenesulfonamide in the form of a white solid (14.9 g, yield: 86%).

2; $^1$H NMR (500 MHz, CDCl$_3$, δ ppm): 1.34 (d, J=6.5 Hz, 3H), 2.64 (d, J=7 Hz, 1H), 3.49-3.52 (m, 1H), 3.57-3.64 (m, 2H), 7.72-7.77 (m, 2H), 7.86-7.89 (m, 1H), 8.16-8.19 (m, 1H). ESI-MS m/z: 261 [M+H]$^+$, 283 [M+Na]$^+$, 543 [2M+Na]$^+$.

3; $^1$H NMR (500 MHz, CDCl$_3$, δ ppm): 1.24 (d, J=7.0 Hz, 3H), 2.99 (s, 3H), 3.87-3.91 (m, 1H), 4.11-4.18 (m, 2H), 5.52 (d, J=8 Hz, 1H), 7.75-7.79 (m, 2H), 7.90-7.92 (m, 1H), 8.16-8.17 (m, 1H). ESI-MS m/z: 339 [M+H]$^+$, 361 [M+Na]', 699 [2M+Na]'.

(2) Steps 3 and 4

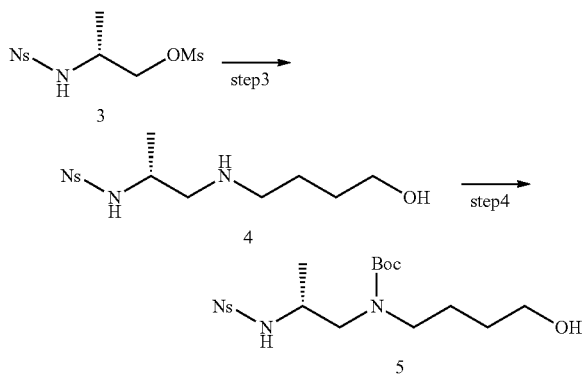

4-amino-1-butanol (636 mg) and potassium carbonate (2.45 g) were suspended in acetonitrile (8 mL), and the suspension was stirred at 70° C. To this was added dropwise (R)—N-(1-methanesulfonyloxypropan-2-yl)-2-nitrobenzenesulfonamide (2.00 g) dissolved in acetonitrile (30 mL) for 60 minutes. The reaction liquid was further stirred at this temperature for 2 hours, disappearance of the raw material was then confirmed by TLC, and the reaction liquid was cooled to room temperature. Water was added to the reaction liquid, and the mixture was extracted with ethyl acetate. The organic layer was dried with anhydrous sodium sulfate, and filtered. Subsequently, the filtrate was concentrated under reduced pressure to obtain (R)—N-[2-(4-hydroxy-butylamino)-1-methylethyl]-2-nitrobenzenesulfonamide as a crude product (2.14 g). To this was added dichloromethane (40 mL), and the mixture was cooled to 0° C. To this were added triethylamine (0.822 mL) and di-tert-butyl dicarbonate (1.28 g), and the mixture was stirred at room temperature for 2 hours. Disappearance of the raw material was confirmed by TLC, 1 N hydrochloric acid cooled to 0° C. was then added, and the organic layer was washed. Subsequently, the organic layer was washed with a saturated sodium hydrogencarbonate solution, dried with anhydrous sodium sulfate, and filtered. Subsequently, the filtrate was concentrated under reduced pressure to obtain (R)-tert-butyl 4-hydroxybutyl-2-(2-nitrophenylsulfonamide)propylcarbamate (2.33 g, yield: 91%).

4; $^1$H NMR (500 MHz, CDCl$_3$, δ ppm): 1.11 (d, J=7.0 Hz, 3H), 1.52-1.55 (m, 2H), 1.58-1.63 (m, 2H), 2.55-2.68 (m, 4H), 3.56-3.61 (m, 3H), 7.72-7.76 (m, 2H), 7.85-7.87 (m, 1H), 8.16-8.18 (m, 1H). ESI-MS m/z: 332 [M+H]$^+$, 354 [M+Na]$^+$, 685 [2M+Na]$^+$.

5; $^1$H NMR (500 MHz, CDCl$_3$, δ ppm): 1.08 (brs, 3H), 1.42-1.57 (m, 13H), 3.05-3.42 (m, 4H), 3.63-3.64 (m, 2H), 3.83 (brs, 1H), 7.72 (brs, 2H), 7.84 (brs, 1H), 8.11 (d, J=7.0 Hz, 1H). ESI-MS m/z: 332 [M-CO$_2$C(CH$_3$)$_3$+H]+, 432 [M+H]$^+$, 454 [M+Na]$^+$, 885 [2M+Na]$^+$.

(3) Step 5

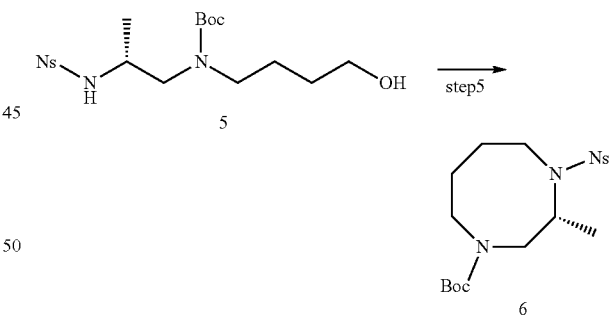

(R)-tert-butyl 4-hydroxybutyl-2-(2-nitrophenylsulfonamide)propylcarbamate (2.33 g) and triphenylphosphine (2.12 g) were dissolved in tetrahydrofuran (20 mL) under the nitrogen flow, and diisopropyl azodicarboxylate (1.60 mL) was added dropwise at 0° C. The reaction liquid was stirred at room temperature for 2 hours, disappearance of the raw material was confirmed by TLC, and the reaction liquid was concentrated under reduced pressure. The obtained residue was washed with hexane, followed by adding ether. The precipitate was removed, and the filtrate was concentrated to obtain (R)-tert-butyl 3-methyl-4-(2-nitrophenylsulfonyl)-1,4-diazocane-1-carboxylate as an orange-colored oily crude product (4.3 g).

6; $^1$H NMR (500 MHz, CDCl$_3$, δ ppm): 0.92, 0.98 (d, J=5.7 Hz, 3H), 1.48 (s, 9H), 1.67-1.77 (m, 2H), 1.85-1.95 (m, 2H), 3.07-3.12 (m, 1H), 3.32-3.50 (m, 4H), 3.69-3.71 (m, 1H), 4.16-4.20 (m, 1H), 7.57-7.59 (m, 1H), 7.64-7.69 (m, 2H), 7.97, 8.02 (d, J=6.5 Hz, 1H). ESI-MS m/z: 414 [M+H]$^+$, 436 [M+Na]$^+$, 849 [2M+Na]$^+$.

(4) Step 6

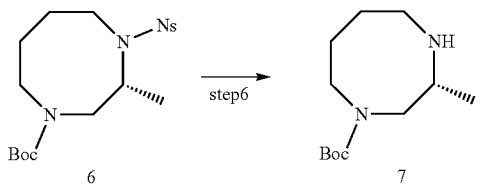

(R)-tert-butyl 3-methyl-4-(2-nitrophenylsulfonyl)-1,4-diazocane-1-carboxylate (4.3 g) was dissolved in acetonitrile (20 mL), and potassium carbonate (4.0 g) was added. To this was added thiophenol (1.2 mL) at room temperature, and the mixture was stirred at 50° C. for 1 hour. Disappearance of the raw material was confirmed by TLC, insoluble materials were then filtered, and the filtrate was concentrated under reduced pressure. 2 N hydrochloric acid was added to the residue to a pH of 3. The mixture was washed with ethyl acetate, and the aqueous layer was adjusted to a pH of about 9 with potassium carbonate, and extracted with ethyl acetate. The organic layer was dried with anhydrous sodium sulfate, and filtered. Subsequently, the filtrate was concentrated under reduced pressure to obtain (R)-tert-butyl 3-methyl-1,4-diazocane-1-carboxylate in the form of a yellow oily material (758 mg, yield in two steps: 61%)

7; $^1$H NMR (500 MHz, CDCl$_3$, δ ppm): 1.04 (d, J=6.0 Hz, 3H), 1.46 (s, 9H), 1.53-1.77 (m, 4H), 2.53-2.70 (m, 2H), 2.99-3.17 (m, 3H), 3.58-3.92 (m, 2H). ESI-MS m/z: 229 [M+H]$^+$.

(5) Step 7

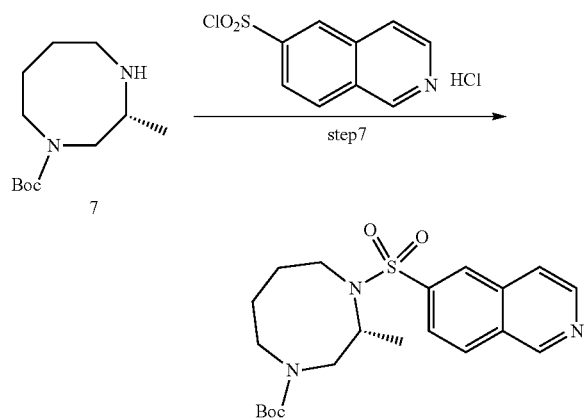

(R)-tert-butyl 3-methyl-1,4-diazocane-1-carboxylate (1.09 g) and triethylamine (1.32 mL) were dissolved in acetonitrile (20 mL), 6-chlorosulfonylisoquinoline hydrochloride (1.26 g) was added under cooling with iced water, and the mixture was stirred for 2 hours under cooling with iced water. Disappearance of the raw material was confirmed by TLC, the reaction product was then concentrated under reduced pressure, water was added, and the mixture was extracted with ethyl acetate. The organic layer was washed with saturated saline, dried with anhydrous sodium sulfate, and then filtered. The filtrate was concentrated under reduced pressure to obtain (R)-tert-butyl 4-(isoquinolin-6-ylsulfonyl)-3-methyl-1,4-diazocane-1-carboxylate in the form of a yellow oily material (2.08 g).

8; $^1$H NMR (500 MHz, CDCl$_3$, δ ppm): 0.82, 0.90 (d, J=6.8 Hz, 3H), 1.48 (s, 9H), 1.73-2.02 (m, 4H), 2.98-3.08 (m, 1H), 3.31-3.51 (m, 4H), 3.60-3.63 (m, 1H), 4.22-4.26 (m, 1H), 7.77 (d, J=4.8 Hz, 1H), 7.91 (d, J=8.5 Hz, 1H), 8.10 (d, J=8.5 Hz, 1H), 8.37 (s, 1H), 8.67 (d, J=4.8 Hz, 1H), 9.35 (s, 1H). ESI-MS m/z: 420 [M+H]$^+$, 839 [2M+H]$^+$, 861 [2M+Na]$^+$.

(7) Step 8

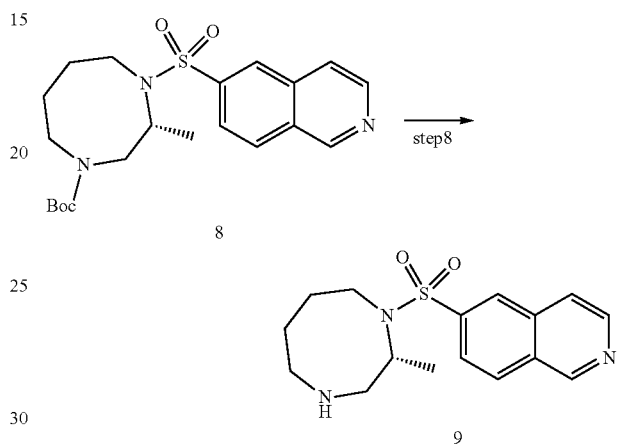

(R)-tert-butyl 4-(isoquinolin-6-ylsulfonyl)-3-methyl-1,4-diazocane-1-carboxylate (2.08 g) was dissolved in ethyl acetate (8 mL), and a 4 M hydrochloric acid/1,4-dioxane solution (12 mL) was added at room temperature. The mixture was stirred at room temperature for 16 hours, and ethyl acetate was then added to wash the solid. The solvent was removed with a pipette, and the remaining solid was dissolved by adding water. This aqueous layer was washed once with ethyl acetate, and then made basic by adding sodium hydroxide. Thereafter, the aqueous layer was extracted with dichloromethane, and dried with anhydrous sodium sulfate. Filtration was performed, and the filtrate was then concentrated under reduced pressure to obtain (R)-6-(2-methyl-1,4-diazocan-1-ylsulfonyl)isoquinoline as a yellow oily material (1.17 g, yield in two steps: 77%).

9; $^1$H NMR (500 MHz, CDCl$_3$, δ ppm): 0.8 (d, J=6.5 Hz, 3H), 1.50-1.65 (m, 2H), 1.89-1.94 (m, 1H), 2.01-2.04 (m, 1H), 2.67-2.71 (m, 1H), 2.77-2.82 (m, 1H), 2.95-3.00 (m, 2H), 3.48-3.59 (m, 2H), 3.97-4.00 (m, 1H), 7.76 (d, J=6.0 Hz, 1H), 7.94 (d, J=8.7 Hz, 1H), 8.10 (d, J=8.7 Hz, 1H), 8.37 (s, 1H), 8.66 (d, J=6.0 Hz, 1H), 9.34 (s, 1H). ESI-MS m/z: 320 [M+H]', 639 [2M+H]'.

(8) Step 9

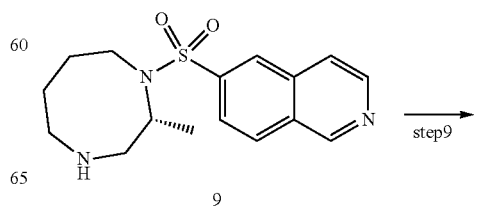

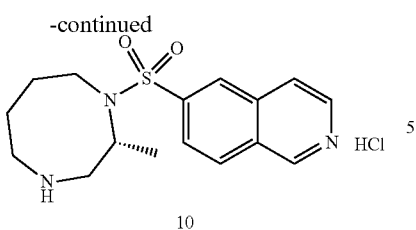

(R)-6-(2-methyl-1,4-diazocan-1-ylsulfonyl)isoquinoline (0.69 g) was dissolved in ethyl acetate (5 mL), 1 M hydrochloric acid/diethyl ether (2.0 mL) was added at room temperature, and the mixture was stirred for 20 hours. The precipitate was washed with ethyl acetate and simultaneously filtered to obtain (R)-6-((2-methyl-1,4-diazocan-1-yl)sulfonyl)isoquinoline hydrochloride in the form of a white solid (0.7 g, yield: 91%).

10;$^1$H NMR (400 MHz, D$_2$O, δ ppm): 0.73 (d, J=6.8 Hz, 3H), 1.82-2.20 (m, 4H), 3.18-3.40 (m, 4H), 3.50-3.60 (m, 1H), 3.72-3.80 (m, 1H), 4.40-4.52 (m, 1H), 7.95 (d, J=6.0 Hz, 1H), 8.0 (dd, J=1.8, 8.7 Hz, 1H), 8.28 (d, J=8.7 Hz, 1H), 8.51 (s, 1H), 8.57 (d, J=6.0 z, 1H), 9.31 (s, 1H). ESI-MS m/z: 320 [M+H]$^+$, 639 [2M+H]$^+$. Anal. calcd for C$_{16}$H$_{22}$ClN$_3$O$_2$S: C, 54.00%; H, 6.23%; N, 11.81%. Found: C, 53.90%; H, 6.23%; N, 11.60%.

Example 2

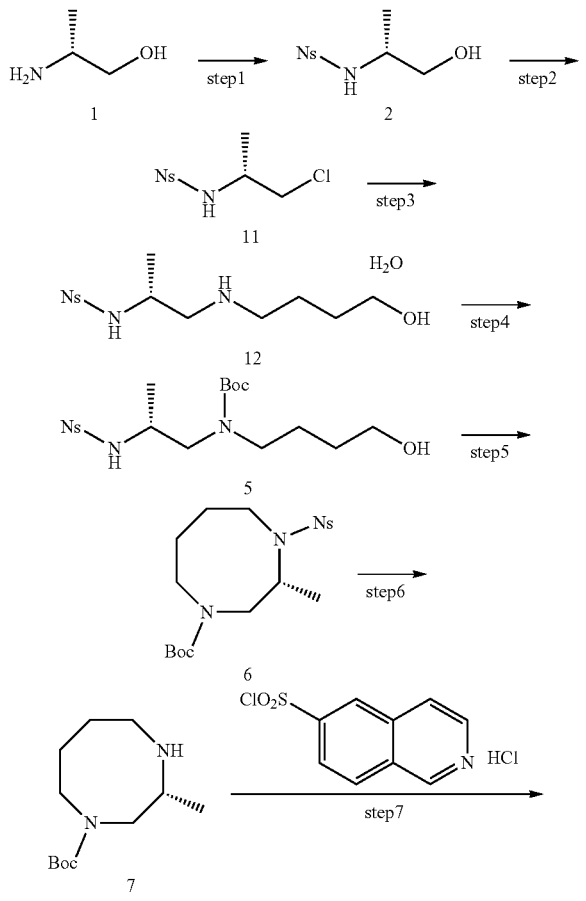

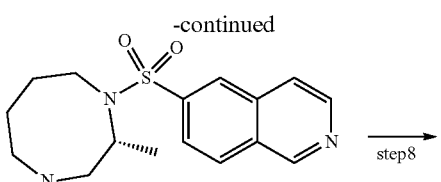

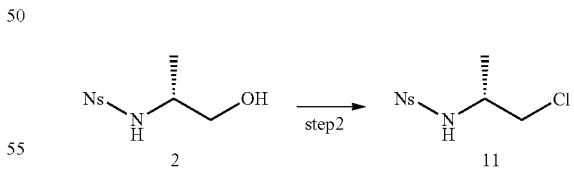

(1) Step 1

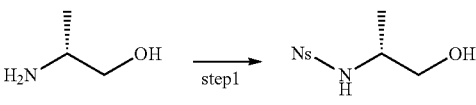

(R)-2-amino-1-propanol (20.0 g) was dissolved in tetrahydrofuran (800 mL), and triethylamine (26.9 g) was added, and the mixture was cooled to 0° C. 2-nitrobenzenesulfonyl chloride (59.0 g) was added, and the mixture was stirred at 25° C. for 3 hours.

After completion of the reaction, water was added, and the mixture was extracted with ethyl acetate. The organic layer was washed with saline, dried with sodium sulfate, and concentrated to obtain (R)—N-(2-hydroxy-1-methylethyl)-2-nitrobenzenesulfonamide (72.1 g).

The NMR spectral data was identical to that in Example 1.

(2) Step 2

Ns—NH—CH(CH$_3$)—CH$_2$OH → Ns—NH—CH(CH$_3$)—CH$_2$Cl

2 → 11

(R)—N-(2-hydroxy-1-methylethyl)-2-nitrobenzenesulfonamide (17.3 g) was dissolved in tetrahydrofuran (40 mL), thionyl chloride (27.7 g) was added, and the mixture was stirred at 60° C. for 5 hours.

After completion of the reaction, the reaction product was brought back to room temperature, toluene was added, and the mixture was concentrated. Toluene was added to the residue, and the precipitate was filtered to obtain (R)—N-(2-chloro-1-methylethyl)-2-nitrobenzenesulfonamide (10.4 g).

11; $^1$H NMR (300 MHz, CDCl$_3$, δ ppm): 1.26 (d, J=6.6 Hz, 3H), 3.55 (d, J=4.4 Hz, 2H), 3.84-3.96 (m, 1H), 5.61 (d, J=7.7 Hz, 1H), 7.74-7.80 (m, 2H), 7.89-7.93 (m, 1H), 8.14-8.18 (m, 1H).

MS m/z:229 [M+H]$^+$

Melting point: 90° C.

IR: 3304, 3281, 1540, 1426, 1357, 1339, 1163, 748, 601, 562 (cm$^{-1}$)

(3) Step 3

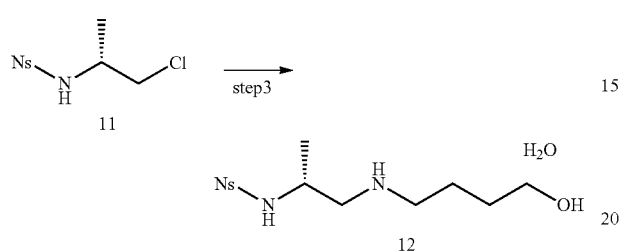

4-amino-1-butanol (5.1 g) was dissolved in acetonitrile (40 mL), potassium carbonate (14.9 g) was added, and the mixture was heated to 70° C. A solution of (R)—N-(2-chloro-1-methylethyl)-2-nitrobenzenesulfonamide (10.0 g) and acetonitrile (70 mL) was added dropwise. After the dropwise addition, the mixture was stirred at 70° C. for 2 hours.

After completion of the reaction, the reaction product was brought back to room temperature, water was added, and the mixture was extracted with acetonitrile. The organic layer was concentrated, ethyl acetate was added to the obtained residue, and the precipitated yellow solid was taken by filtration to obtain (R)—N-[2-(4-hydroxy-butylamino)-1-methylethyl]-2-nitrobenzenesulfonamide monohydrate (7.8 g).

12; $^1$H NMR (300 MHz, CDCl$_3$, δ ppm): 1.10 (d, J=7.0 Hz, 3H), 1.50-1.65 (m, 4H), 2.55-2.70 (m, 4H), 3.55-3.64 (m, 3H), 7.72-7.79 (m, 2H), 7.83-7.88 (m, 1H), 8.16-8.20 (m, 1H).

MS m/z: 332 [M+H]$^+$

Melting point: 58° C. (decomposition)

IR: 3331, 1533, 1371, 1172, 1156, 908, 855, 655 (cm-1)

(4) Steps 4 to 9

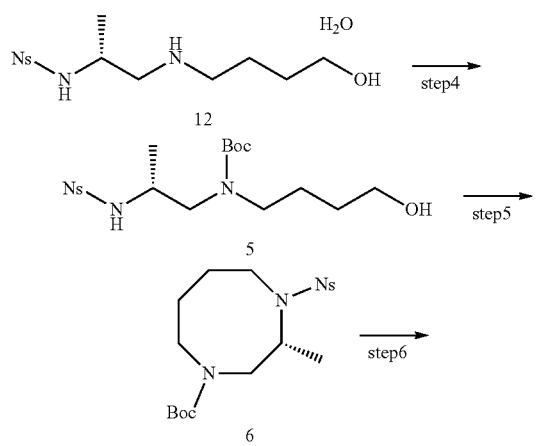

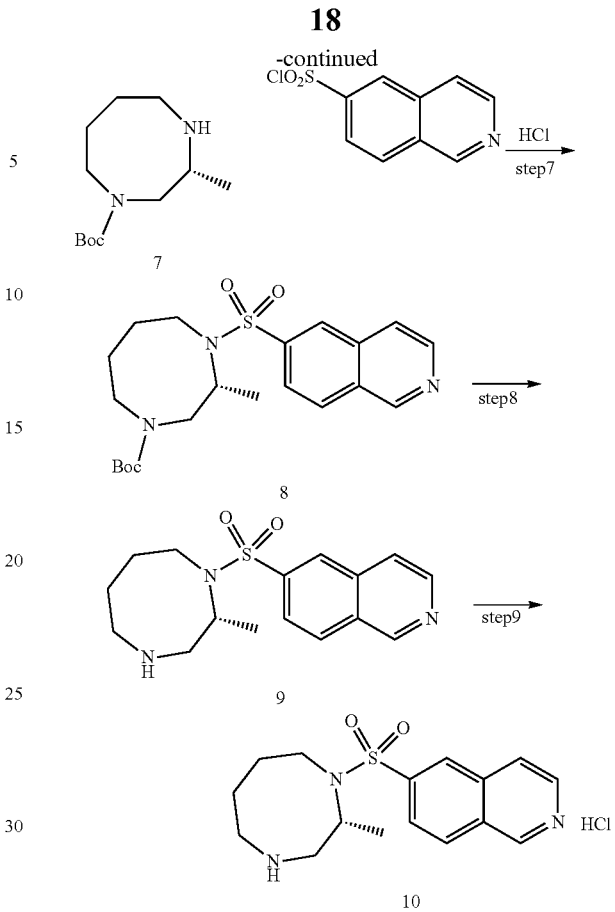

Step 4

(R)—N-[2-(4-hydroxy-butylamino)-1-methylethyl]-2-nitrobenzenesulfonamide monohydrate (100 g) was dissolved in methanol (570 mL), a solution of triethylamine (41.5 g) and di-tert-butyl dicarbonate (89.6 g) in methanol (75 mL) was added dropwise, the mixture was stirred at 15° C. for 1 hour.

After completion of the reaction, the reaction product was concentrated, water was added, and the mixture was extracted with toluene. The organic layer was washed with 10% saline, and concentrated. The obtained toluene solution of (R)-tert-butyl 4 hydroxybutyl-2-(2-nitrophenylsulfonamide)propylcarbamate (372 g) was successively used for the subsequent reaction.

The NMR spectral data was identical to that in Example 1.

Step 5

A liquid obtained by dissolving triphenylphosphine (179 g) in toluene was added to the toluene solution of (R)-tert-butyl 4 hydroxybutyl-2-(2-nitrophenylsulfonamide)propylcarbamate (372 g). The liquid was added dropwise to a solution of diisopropyl azodicarboxylate (84.4 g) in toluene (550 mL). After completion of the dropwise addition, the mixture was stirred at 0° C. for 15 hours, and the precipitate was filtered. The filtrate was concentrated. The obtained toluene solution of (R)-tert-butyl 3-methyl-4-(2-nitrophenylsulfonyl)-1,4-diazocane-1-carboxylate (1,235 g) was used for the subsequent reaction.

The NMR spectral data was identical to that in Example 1.

Step 6

Dodecanthiol (83.9 g) was dissolved in N,N-dimethylformamide (800 mL), and lithium hydroxide monohydrate (47.9 g) was added. To this was added dropwise the toluene solution of (R)-tert-butyl 3-methyl-4-(2-nitrophenylsulfonyl)-1,4-diazocane-1-carboxylate (1,235 g). After completion of the dropwise addition, the mixture was stirred at 25° C. for 1 hour.

After completion of the reaction, the reaction product was washed with water. 1 N hydrochloric acid was added to the organic layer, and the mixture was extracted with water. Potassium carbonate was added to aqueous layer, the mixture was extracted with toluene, and the organic layer was concentrated. The obtained toluene solution of (R)-tert-butyl 3-methyl-1,4-diazocane-1-carboxylate (195 g) was used for the subsequent reaction.

The NMR spectral data was identical to that in Example 1.

Step 7

Triethylamine (31.7 g), 4-dimethylaminopyridine (0.2 g), toluene (510 mL) and N,N-dimethylformamide (350 mL) were added to the toluene solution of (R)-tert-butyl 3-methyl-1,4-diazocane-1-carboxylate (174 g), and the mixture was cooled to 0° C. 6-chlorosulfonylisoquinoline hydrochloride (41.3 g) was added, and the mixture was stirred at 0° C. for 2 hours.

After completion of the reaction, the reaction product was washed with water. The obtained toluene solution of (R)-tert-butyl 4-(isoquinolin-6-ylsulfonyl)-3-methyl-1,4-diazocane-1-carboxylate (827 g) was used for the subsequent reaction.

The NMR spectral data was identical to that in Example 1.

Step 8

10% sulfuric acid (600 g) was added to the toluene solution of (R)-tert-butyl 4-(isoquinolin-6-ylsulfonyl)-3-methyl-1,4-diazocane-1-carboxylate (825 g), and the mixture was stirred at 20° C. for 15 hours.

After completion of the reaction, the liquid was separated, a 10% sodium hydroxide aqueous solution was added to the aqueous layer, and the mixture was extracted with ethyl acetate. The obtained ethyl acetate solution of (R)-6-((2-methyl-1,4-diazocan-1-yl)sulfonyl)isoquinoline (824 g) was used for the subsequent reaction.

The NMR spectral data was identical to that in Example 1.

Step 9

Methanol (360 mL) was added to the ethyl acetate solution of (R)-6-((2-methyl-1,4-diazocan-1-yl)sulfonyl)isoquinoline (812 g), and the mixture was cooled to 5° C. To this was added dropwise a solution of 35% hydrochloric acid (9.3 g) in methanol (30 mL), and the mixture was stirred at 2° C. for 20 hours. The precipitated yellowish white solid was taken by filtration to obtain (R)-6-((2-methyl-1,4-diazocan-1-yl)sulfonyl)isoquinoline hydrochloride (26.7 g).

The NMR spectral data was identical to that in Example 1.

Example 3

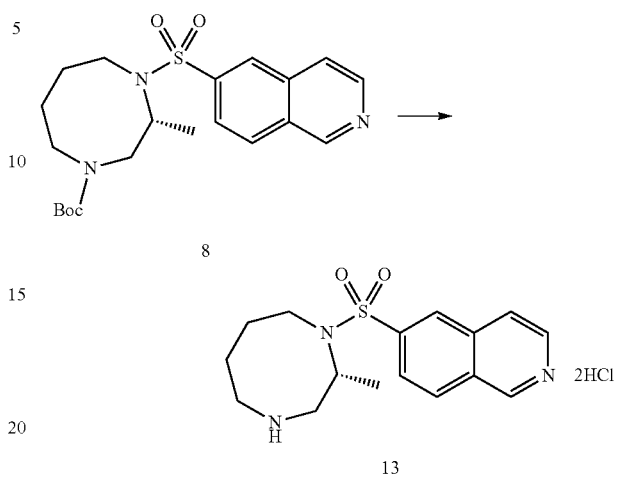

(R)-tert-butyl 4-(isoquinolin-6-ylsulfonyl)-3-methyl-1,4-diazocane-1-carboxylate (0.100 g) was dissolved in ethyl acetate (1.5 mL) and methanol (3.0 mL), and a 4 M hydrochloric acid/ethyl acetate solution (0.6 mL) was added at room temperature. The mixture was stirred at room temperature for 3 days, and ethyl acetate was then added to precipitate a solid. The precipitate was washed with ethyl acetate and simultaneously filtered to obtain (R)-6-((2-methyl-1,4-diazocan-1-yl)sulfonyl)isoquinoline dihydrochloride in the form of a white solid (0.092 g, yield: 99%). 13; $^1$H NMR (400 MHz, $D_2O$, δ ppm): 0.74 (d, J=6.6 Hz, 3H), 1.82-2.18 (m, 4H), 3.20-3.39 (m, 4H), 3.48-3.58 (m, 1H), 3.72-3.81 (m, 1H), 4.42-4.56 (m, 1H), 8.24 (dd, J=1.8, 8.8 Hz, 1H), 8.34 (d, J=6.2 Hz, 1H), 8.53 (d, J=8.8 Hz, 1H), 8.64 (d, J=6.2 Hz, 1H), 8.75 (s, 1H), 9.61 (s, 1H). ESI-MS m/z: 320 [M+H]$^+$, 639 [2M+H]$^+$.

The invention claimed is:

1. A method for producing an isoquinoline-6-sulfonamide derivative of the following formula (11), optionally as a salt:

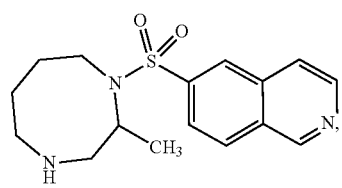

(11)

the method comprising:
reacting a 1,4-diazocane compound of the following formula (8), optionally as a salt:

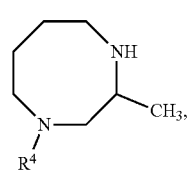

(8)

wherein $R^4$ is an amino protecting group, with an isoquinoline-6-sulfonyl halide of the following formula (9), optionally as a salt:

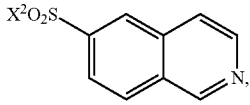

(9)

wherein $X^2$ is a halogen atom; and
then carrying out an elimination reaction of the amino protecting group.

2. The method of claim 1, further comprising producing a 1,4-diazocane compound of the following formula (A):

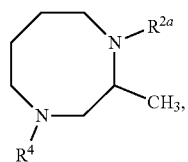

(A)

wherein $R^{2a}$ represents a hydrogen atom or an amino protecting group and $R^4$ represents an amino protecting group, or a salt thereof, the method comprising:

reacting a compound of the following formula (6):

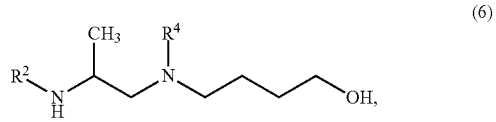

(6)

wherein $R^2$ and $R^4$ each represent an amino protecting group, with an azodicarboxylic acid ester and triphenylphosphine, and then carrying out an elimination reaction of amino protecting group.

* * * * *